(12) United States Patent
Nakasho

(10) Patent No.: US 9,291,546 B2
(45) Date of Patent: Mar. 22, 2016

(54) OBSERVED PORTION FIXING APPARATUS AND MICROSCOPE

(71) Applicant: OLYMPUS CORPORATION, Shibuya-ku, Tokyo (JP)

(72) Inventor: Eiji Nakasho, Kyoto (JP)

(73) Assignee: OLYMPUS CORPORATION, Tokyo (JP)

( * ) Notice: Subject to any disclaimer, the term of this patent is extended or adjusted under 35 U.S.C. 154(b) by 95 days.

(21) Appl. No.: 13/893,084

(22) Filed: May 13, 2013

(65) Prior Publication Data
US 2014/0063599 A1 Mar. 6, 2014

(30) Foreign Application Priority Data
Sep. 3, 2012 (JP) .................. 2012-192776

(51) Int. Cl.
G02B 21/26 (2006.01)
G01N 21/01 (2006.01)
G02B 21/33 (2006.01)

(52) U.S. Cl.
CPC ............... *G01N 21/01* (2013.01); *G02B 21/33* (2013.01)

(58) Field of Classification Search
USPC .................................................. 359/391, 383
See application file for complete search history.

(56) References Cited

U.S. PATENT DOCUMENTS

| | | | | |
|---|---|---|---|---|
| 5,870,223 A * | 2/1999 | Tomimatsu | ................ | 359/392 |
| 7,333,265 B2 * | 2/2008 | Hasegawa et al. | ............. | 359/368 |
| 7,372,538 B2 * | 5/2008 | Binnard | ....................... | 355/30 |
| 2007/0127135 A1 * | 6/2007 | Nagasaka | ................... | 359/665 |
| 2008/0030849 A1 * | 2/2008 | Fukuyama | ......... | G02B 21/0012 359/381 |
| 2008/0174859 A1 * | 7/2008 | Tanikawa | ............. | A61B 5/0059 359/368 |
| 2008/0252967 A1 * | 10/2008 | Tomioka et al. | .............. | 359/398 |
| 2008/0259446 A1 * | 10/2008 | Komatsu et al. | .............. | 359/391 |
| 2010/0067104 A1 * | 3/2010 | Lippert et al. | ................ | 359/391 |
| 2011/0043905 A1 * | 2/2011 | Mitzkus et al. | ............... | 359/383 |

FOREIGN PATENT DOCUMENTS

| JP | 2005-338631 A | 12/2005 |
|---|---|---|
| JP | 2008-286883 A | 11/2008 |

OTHER PUBLICATIONS

Mark R. Looney et al: "Stabilized imaging of immune surveillance in the mouse lung": Nature Methods: vol. 8, No. 1: Jan. 2011: pp. 91-98 (in English).

* cited by examiner

*Primary Examiner* — Bumsuk Won
*Assistant Examiner* — Balram Parbadia
(74) *Attorney, Agent, or Firm* — Holtz, Holtz & Volek PC

(57) ABSTRACT

An immersion liquid retainer is an immersion liquid retainer used for an observation made with a microscope including an immersion objective. The immersion liquid retainer includes a fixing part in which a first penetration hole for viewing an observed portion of a specimen is formed and which is fixed to the specimen, and an immersion liquid retaining part where a concave part that has a bottom surface configured with a transparent flat plate and is intended to retain an immersion liquid is formed. The immersion liquid retaining part is joined to the fixing part or formed integrally with the fixing part so that the transparent flat plate covers the first penetration hole.

9 Claims, 19 Drawing Sheets

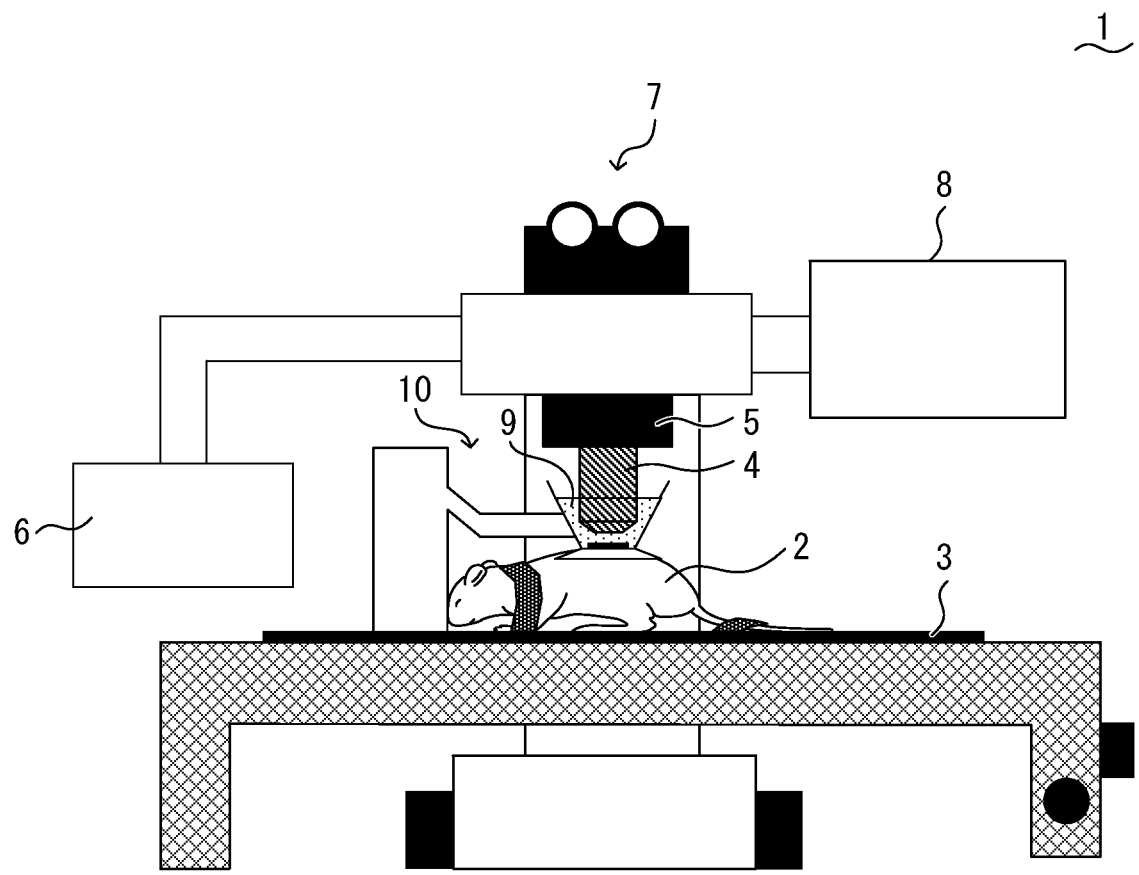
F I G. 1

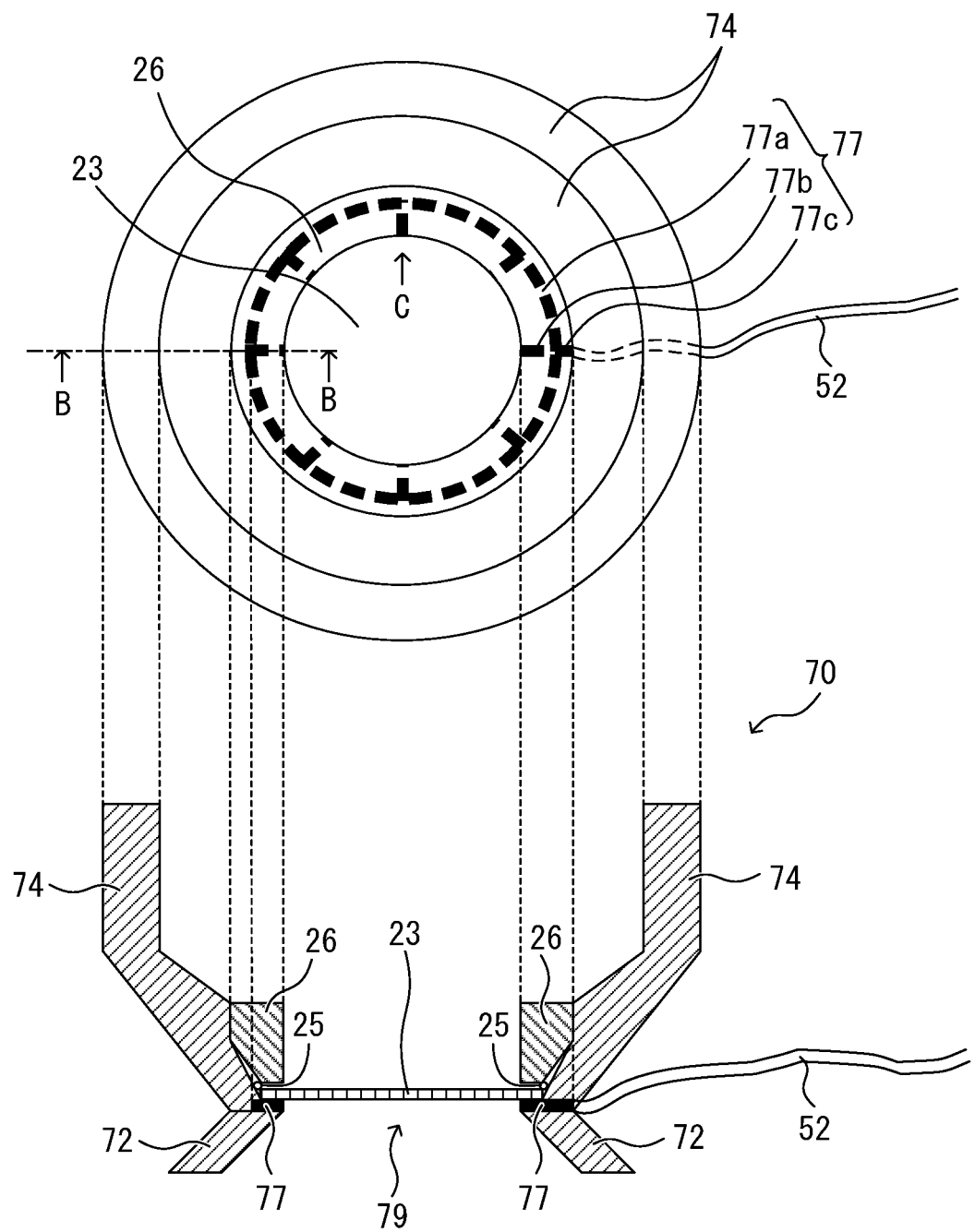
F I G. 8A

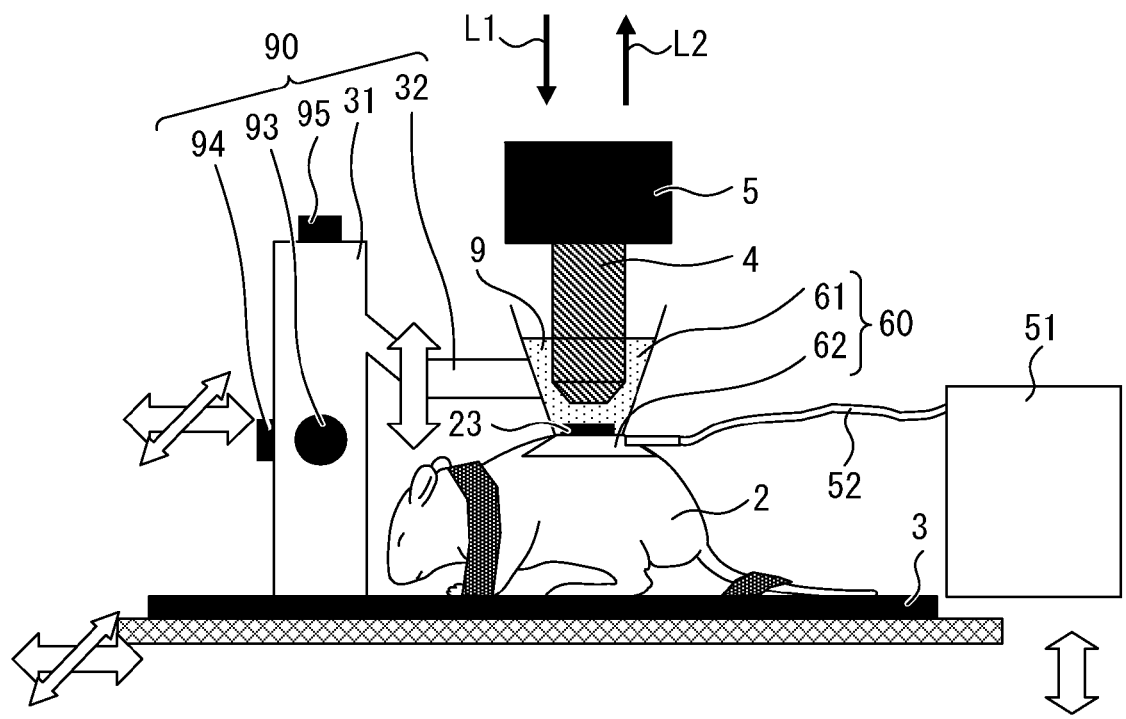
F I G. 9

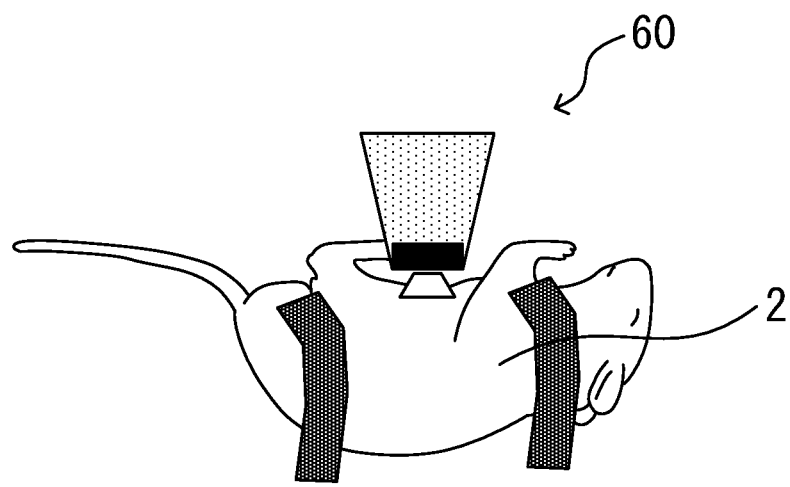
F I G. 10C

OBSERVED PORTION FIXING APPARATUS AND MICROSCOPE

CROSS-REFERENCE TO RELATED APPLICATIONS

This application is based upon and claims the benefit of priority from prior Japanese Patent Application No. 2012-192776, filed on Sep. 3, 2012, the entire contents of which are incorporated herein by this reference.

BACKGROUND OF THE INVENTION

1. Field of the Invention

The present invention relates to an immersion liquid retainer and an observed portion fixing apparatus, which are used to observe a laboratory animal alive for a long duration with a microscope including an immersion objective, and to a microscope including the retainer and the apparatus.

2. Description of the Related Art

Multi-photon excitation microscopes such as a two-photon excitation microscope and the like enable a laboratory animal such as a mouse or the like to be observed alive. In recent years, also a time-lapse observation for observing a laboratory animal alive for a long duration equal to or longer than several hours has been made. Such an observation is normally conducted in a state where a laboratory animal is made asleep. However, since a field of view and a focal depth of a microscope are very narrow, it is needed to suppress movements of an observed portion, caused by breathing, heartbeat or the like, of a laboratory animal so as to continuously observe the same portion of the animal.

A technique of suppressing movements of an observed portion of a laboratory animal is disclosed, for example, by Japanese Laid-open Patent Publication No. 2005-338631. Japanese laid-open Patent Publication No. 2005-338631 discloses a microscopy system including a stabilizer for suppressing dynamic behaviors of a surface of a specimen. The microscopy system disclosed by Japanese Laid-open Patent Publication No. 2005-338631 further includes absorption means for absorbing the stabilizer onto a surface of a specimen, so that dynamic behaviors of the surface of the specimen in the neighborhood of the absorbed portion can be suppressed.

SUMMARY OF THE INVENTION

One aspect of the present invention provides an immersion liquid retainer that is used for an observation made with a microscope including an immersion objective, and includes a fixing part in which a first penetration hole for viewing an observed portion of a specimen is formed and which is fixed to the specimen, and an immersion liquid retaining part where a concave part that has a bottom surface configured with a transparent flat plate and is intended to retain an immersion liquid is formed. The immersion liquid retaining part is joined to the fixing part or formed integrally with the fixing part so that the transparent flat plate covers the first penetration hole.

Another aspect of the present invention provides an observed portion fixing apparatus including the immersion liquid retainer according to the above described aspect, and a support part, provided on a stage where the specimen is placed, for supporting the immersion liquid retainer.

A further aspect of the present invention provides a microscope including the observed portion fixing apparatus according to the above described aspect, an immersion objective immersed in an immersion liquid retained in the immersion liquid retaining part of the observed portion fixing apparatus, and a stage where a specimen is placed.

BRIEF DESCRIPTION OF THE DRAWINGS

The present invention will be more apparent from the following detailed description when the accompanying drawings are referenced.

FIG. 1 illustrates a configuration of a microscope according to a first embodiment of the present invention;

FIG. 8A illustrates a configuration of a modification example of the immersion liquid retainer according to the second embodiment of the present invention;

FIG. 9 illustrates a configuration of an observed portion fixing apparatus according to a third embodiment of the present invention;

FIG. 10C illustrates a further example of the attached position of the immersion liquid retainer.

DESCRIPTION OF THE EMBODIMENTS

<First Embodiment>

Figure 2:
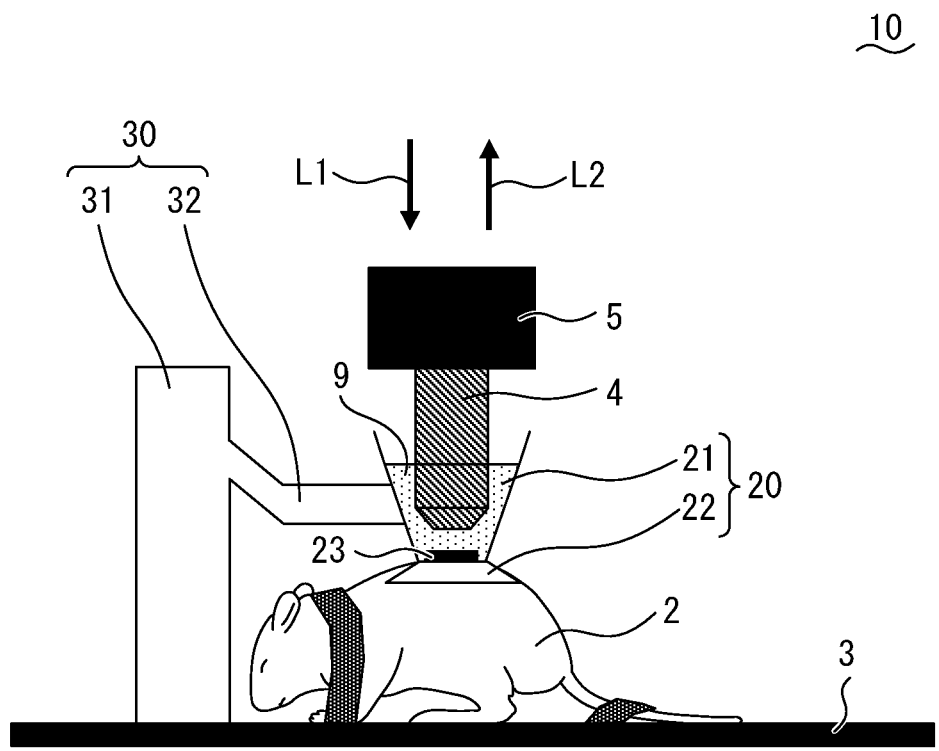
FIG. 2 illustrates a configuration of an observed portion fixing apparatus according to the first embodiment of the present invention.

FIG. 1 illustrates a configuration of a microscope according to a first embodiment. The microscope 1 illustrated in FIG. 1 is a two-photon excitation microscope including an immersion objective 4, and is an erect microscope for observing a live mouse 2, which is a specimen, from above in a sleep state. The microscope 1 is configured to be operable as a time-lapse unit for recording time-varying changes of an observed portion of the mouse 2.

The microscope 1 includes an observed portion fixing apparatus 10 for fixing the observed portion of the mouse 2 in order to continuously observe the same portion of the live mouse 2. The observed portion fixing apparatus 10 plays a role in retaining an immersion liquid 9 that fills a space between the mouse 2 and the immersion objective 4 in order to enable a long-duration observation using the immersion objective 4. Most generally, the immersion liquid 9 is water. However, the immersion liquid used is not limited to water, and other immersion liquids such as silicone oil or the like may be used.

The microscope 1 further includes a stage 3 on which the mouse 2 is placed, a nose piece 5 movable in a Z direction where the immersion objective 4 is attached, a laser light source 6 for emitting excitation light irradiated on the mouse 2, an eyepiece part 7 for viewing a fluorescent image obtained by forming an image of fluoresce from the mouse 2, and a detector 8 for detecting the fluorescence from the mouse 2 and for converting the fluorescence into an electric signal in order to generate image data of the fluorescent image. Note that the stage 3 is configured to be movable in an XY direction orthogonal to an optical axis of the immersion objective 4. More preferably, the stage 3 is configured to be movable also in a Z direction parallel to the optical axis of the immersion objective 4. The microscope 1 may be connected to a personal computer (PC) not illustrated, and the PC may, for example, control components of the microscope 1 and generate image data. Moreover, the stage 3 is provided with a belt for fixing the mouse, and a heater function. With the heater function, a long-duration observation can be more easily made by keeping a temperature of the mouse warm.

FIG. 2 illustrates a configuration of the observed portion fixing apparatus according to this embodiment. The configuration of the observed portion fixing apparatus 10 included in the microscope 1 is described in further detail with reference to FIG. 2.

As illustrated in FIG. 2, the observed portion fixing apparatus 10 includes an immersion liquid retainer 20 for retaining the immersion liquid 9, and a support part 30 for supporting the immersion liquid retainer 20. The support part 30 is provided on the stage 3 where the mouse 2 is placed.

The immersion liquid retainer 20 further includes an immersion liquid retaining part 21 and a fixing part 22. The immersion liquid retaining part 21 plays a role in retaining the immersion liquid 9, and takes, as a whole, the shape of a bowl where a concave surface is orientated toward the side of the objective lens. In the immersion liquid retaining part 21, a concave part where a bottom surface is configured with a cover glass 23 is formed to retain the immersion liquid 9, and the immersion liquid 9 of at least 1 cc can be stored in the concave part. Moreover, an inner diameter of the concave part is formed to be larger than an outer diameter of a tip portion of the immersion objective 4 so that the tip of the immersion objective 4 can be immersed in the immersion liquid 9. In the meantime, the fixing part 22 plays a role in fixing the observed portion of the mouse 2, and is configured to be fixed to the mouse 2 by making direct contact with the mouse 2. In the fixing part 22, a penetration hole (first penetration hole) for viewing the observed portion of the mouse 2 in a state where the fixing part 22 is fixed to the mouse 2 is formed. The fixing part 22 takes, as a whole, the shape of a bowl where a concave part provided with a penetration hole in a bottom surface is orientated toward the side of the specimen. To tightly fix the observed portion of the mouse 2 by securing a surface of a sufficient size to make contact with the mouse 2, it is preferable that an area of the concave surface is of at least 1 mm$^2$ or larger.

The immersion liquid retaining part 21 is joined to the fixing part 22 so that the cover glass 23 covers the penetration hole. Accordingly, excitation light L1 emitted from the laser light source 6 passes through the cover glass 23, which is a transparent flat plate, from the side of the immersion objective 4 toward the side of the mouse 2, and is irradiated on the mouse 2. In the meantime, fluorescence L2 generated from the mouse 2 by irradiating the excitation light passes through the cover glass 23 from the side of the mouse 2 toward the side of the immersion objective 4, and is guided to the eyepiece part 7 or the detector 8.

The support part 30 includes a support part main body 31 provided on the stage 3, and an arm part 32 for supporting the immersion liquid retainer 20 extending from the support part main body 31. The immersion liquid retainer 20 is provided on the stage 3 via the support part 30 by being pressed against the mouse 2 by the support part 30, so that the observed portion fixing apparatus 10 can fix the observed portion of the mouse 2. In the arm part 32, the immersion liquid retainer 20 is configured to be attachable/detachable. An arbitrary immersion liquid retainer in a different size or shape according to the size or the shape of a laboratory animal can be attached.

Figure 3A:
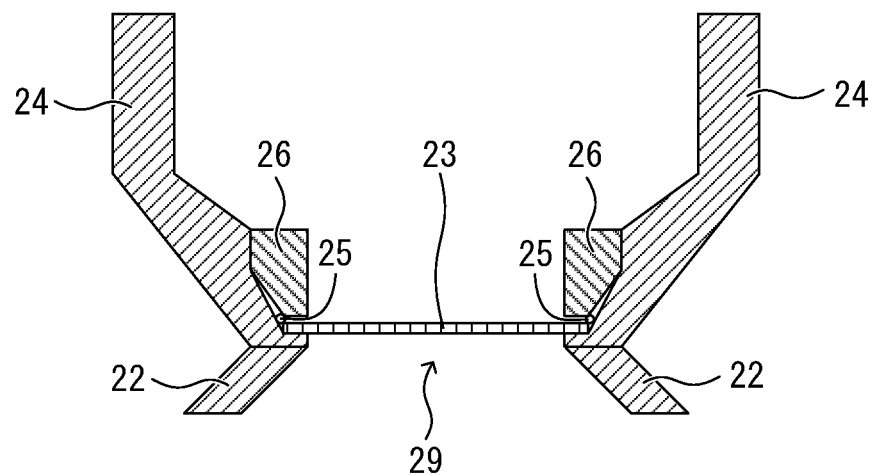
FIG. 3A is a cross-sectional view of an immersion liquid retainer according to the first embodiment of the present invention.
Figure 3B:
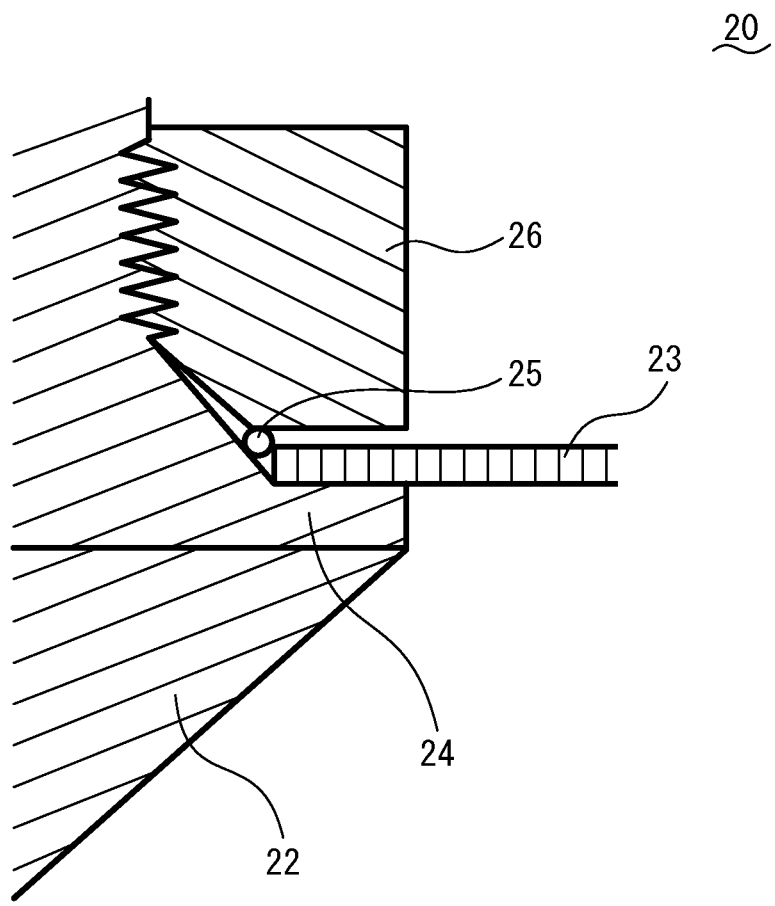
FIG. 3B is a cross-sectional view of an enlarged portion of the immersion liquid retainer illustrated in FIG. 3A.

FIG. 3A is a cross-sectional view of the immersion liquid retainer according to this embodiment. FIG. 3B is a cross-sectional view of an enlarged portion of the immersion liquid retainer illustrated in FIG. 3A. A configuration of the immersion liquid retainer 20 included in the observed portion fixing apparatus 10 is described in further detail with reference to FIGS. 3A and 3B.

The immersion liquid retaining part 21 is configured by including the cover glass 23 that configures the bottom surface of the concave part, an immersion liquid retaining part main body 24 that configures at least a side surface of the concave part, an O-shaped ring 25 for blocking a gap between the cover glass 23 and the immersion liquid retaining part main body 24, and a pressing member 26 for pressing the O-shaped ring 25 against the cover glass 23 and the immersion liquid retaining part main body 24.

The immersion liquid retaining part main body 24 is a circular member into which the tip of the immersion objective 4 can be inserted. On a portion of the bottom surface of the concave part formed in the immersion liquid retaining part main body 24, a penetration hole having nearly the same diameter as the penetration hole 29 (first penetration hole) for viewing the observed portion of the mouse 2, which is formed in the fixing part 22, is formed. In the immersion liquid retainer 20, the cover glass 23 is arranged on the bottom surface of the concave part of the immersion liquid retaining part main body 24, and the penetration hole 29 and a penetration hole that is formed in the immersion liquid retaining part main body 24 and has nearly the same diameter as the penetration hole 29 are covered, so that the space on the side of the fixing part 22 and that on the side of the immersion liquid retaining part main body 24 (immersion liquid retaining part 21) are separated. Both the O-shaped ring 25 and the pressing member 26 are circular members similarly to the immersion liquid retaining part main body 24. The O-shaped ring 25 arranged to block the gap between the cover glass 23 and the immersion liquid retaining part main body 24 plays a role in preventing the immersion liquid 9 from leaking into the space on the side of the fixing part 22. As illustrated in FIG. 3B, a male screw formed in the pressing member 26 is engaged with a female screw formed on an inner side of the immersion liquid retaining part main body 24, and the pressing member 26 presses the O-shaped ring 25 against the cover glass 23 and the immersion liquid retaining part main body 24, whereby the immersion liquid 9 can be securely prevented from leaking into the space on the side of the fixing part 22.

The immersion liquid retainer 20 configured as described above is fixed to the mouse 2 so that the cover glass 23 makes contact with the observed portion of the mouse 2. The immersion liquid retainer 20 can stably retain a large quantity of the immersion liquid 9 in the concave part of the immersion liquid retaining part 21 as illustrated in FIGS. 1 and 2. Therefore, the immersion liquid 9 the amount of which is needed for an observation can be retained for a long duration. Accordingly, with the immersion liquid retainer 20, the gap between the immersion objective 4 and the cover glass 23 can be filled with the immersion liquid 9 without adding the immersion liquid 9 during an observation period even if the observation is continued for a long duration. In contrast, with conventional microscopes, an observation is made in a state where an immersion liquid is retained with a surface tension between an immersion objective and a specimen (or a cover glass). However, an immersion liquid the quantity of which is as small as that retainable with a surface tension can possibly evaporate during an observation period of a log-duration time-lapse observation. Moreover, the shape of a surface of a laboratory animal such as the live mouse 2 or the like is not flat unlike a slice preparation. Therefore, in the conventional microscopes for retaining an immersion liquid with a surface tension, it is difficult to supply a large quantity of an immersion liquid in advance for possible evaporation.

Additionally, in the observed portion fixing apparatus 10 including the immersion liquid retainer 20, the immersion liquid retainer 20 is supported by the support part 30 provided on the stage 3. Therefore, the mouse 2 can be tightly pressed onto the stage 3 with the immersion liquid retainer 20. Accordingly, with the observed portion fixing apparatus 10, the immersion liquid 9 can be retained for a long duration, and movements of an observed portion, which are caused by breathing, heartbeat or the like of the mouse 2, which occur during an observation period, can be suppressed.

Accordingly, with the microscope 1 including the observed portion fixing apparatus 10, the immersion liquid 9 can be retained for a long duration while suppressing movements of an observed portion, which are caused by breathing, heartbeat or the like, whereby the same portion of the mouse 2 can be continuously observed with high resolution for a long duration. Therefore, a time-lapse observation for a long duration equal to or longer than several hours can be made without the need for adding the immersion liquid 9 by an observer during an observation period, so that a burden imposed on the observer can be significantly reduced. Moreover, for example, a situation where the observed portion is out of a focal depth of the objective lens due to a temperature change of the immersion liquid or a physically applied pressure as a result of supplying the immersion liquid can be prevented from occurring.

Figure 4A:
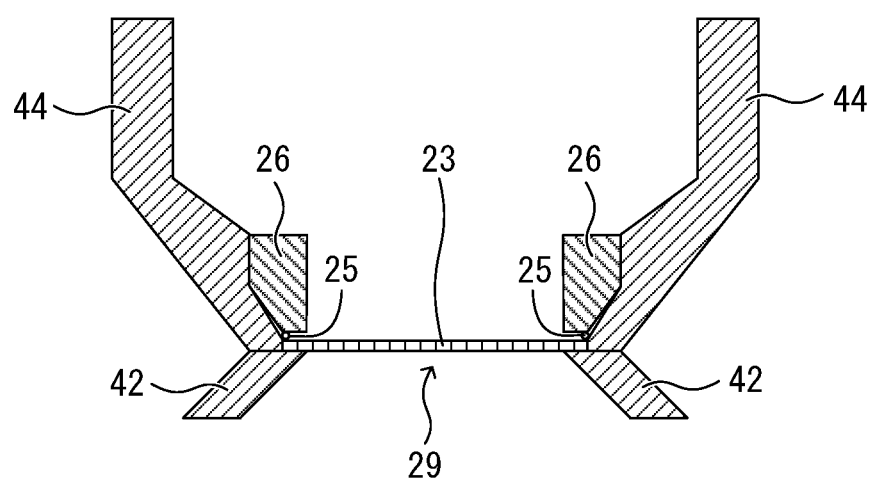
FIG. 4A is a cross-sectional view of a modification example of the immersion liquid retainer according to the first embodiment of the present invention.
Figure 4B:
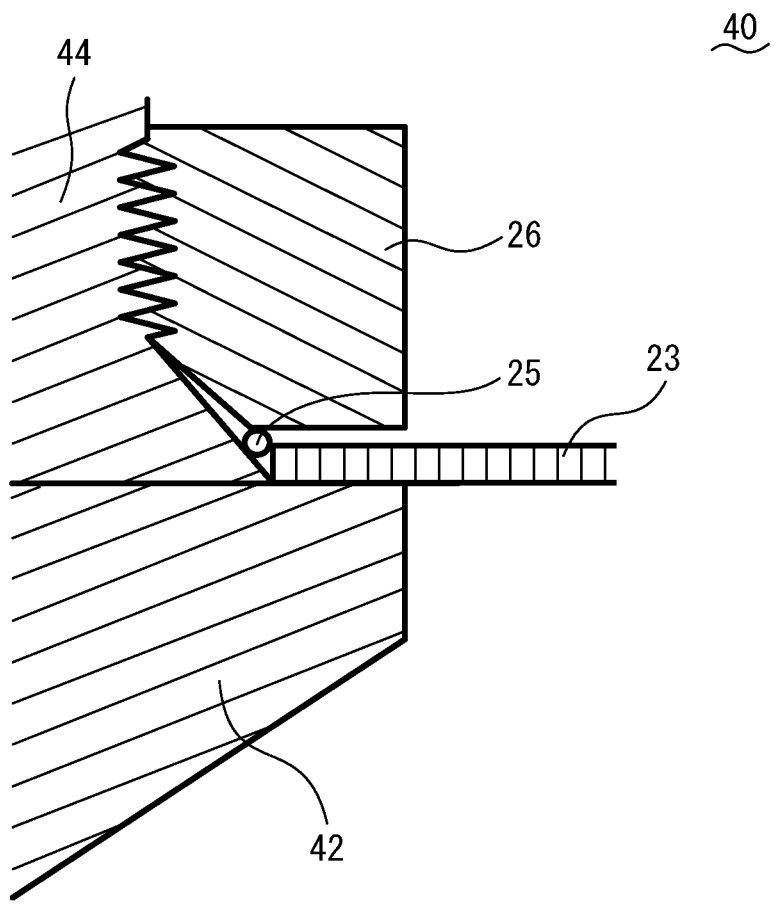
FIG. 4B is a cross-sectional view of an enlarged portion of the modification example of the immersion liquid retainer illustrated in FIG. 4A.
Figure 5:
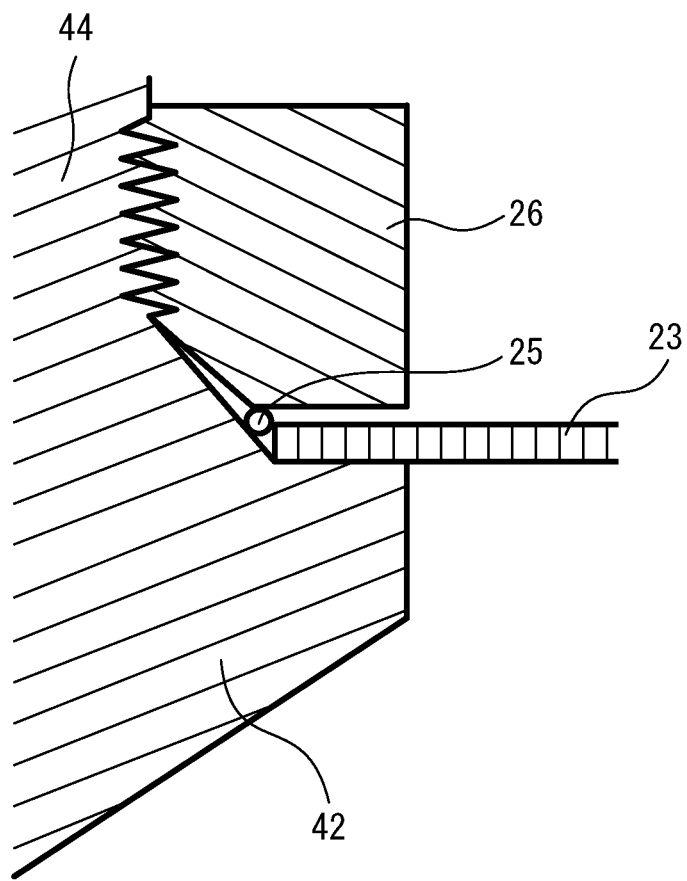
FIG. 5 is a cross-sectional view of an enlarged portion of another modification example of the immersion liquid retainer according to the first embodiment of the present invention.

FIGS. 3A and 3B illustrate the example where the cover glass 23 is arranged on the bottom surface of the concave part of the immersion liquid retaining part main body 24. However, the cover glass 23 may be arranged on a joint surface of a fixing part 42 joined to an immersion liquid retaining part main body 44 as illustrated in FIGS. 4A and 4B. The cover glass 23 may be arranged to cover the penetration hole 29, and may configure the bottom surface of the concave part formed on the immersion liquid retaining part. Moreover, the immersion liquid retaining part main body 44 and the fixing part 42 may be formed integrally in advance as illustrated in FIG. 5.

As a result, the joint operation of the immersion liquid retaining part main body 44 and the fixing part 42 can be omitted.

Additionally, in the immersion liquid retainer 20 illustrated in FIGS. 3A and 3B and the immersion liquid retainer 40 illustrated in FIGS. 4A and 4B, the cover glass 23 is fixed by engaging the immersion liquid retaining part main body with the pressing member 26. Such a configuration is preferable since the cover glass 23 can be easily removed from the immersion liquid retainer and cleansed after an observation is made. Note that the cover glass 23 may be fixed with an arbitrary method that can remove the cover glass 23. Moreover, if the immersion liquid retainer is designed to be disposable, the cover glass 23 may be fixed to the immersion liquid retaining part main body with an adhesive.

Furthermore, the example where only the cover glass 23 that the excitation light L1 and the fluorescence L2 pass through is made of a transparent material among the components of the immersion liquid retainer 20 is provided above. However, the other components that configure the immersion liquid retainer 20 may be made of a transparent material. As a result, an observed portion can be visually examined through the fixing part 22 and the like even when the immersion liquid retainer 20 is attached to the mouse 2. Accordingly, operations such as a fine adjustment and the like of an attached position of the immersion liquid retainer 20 are facilitated.

<Second Embodiment>

Figure 6:
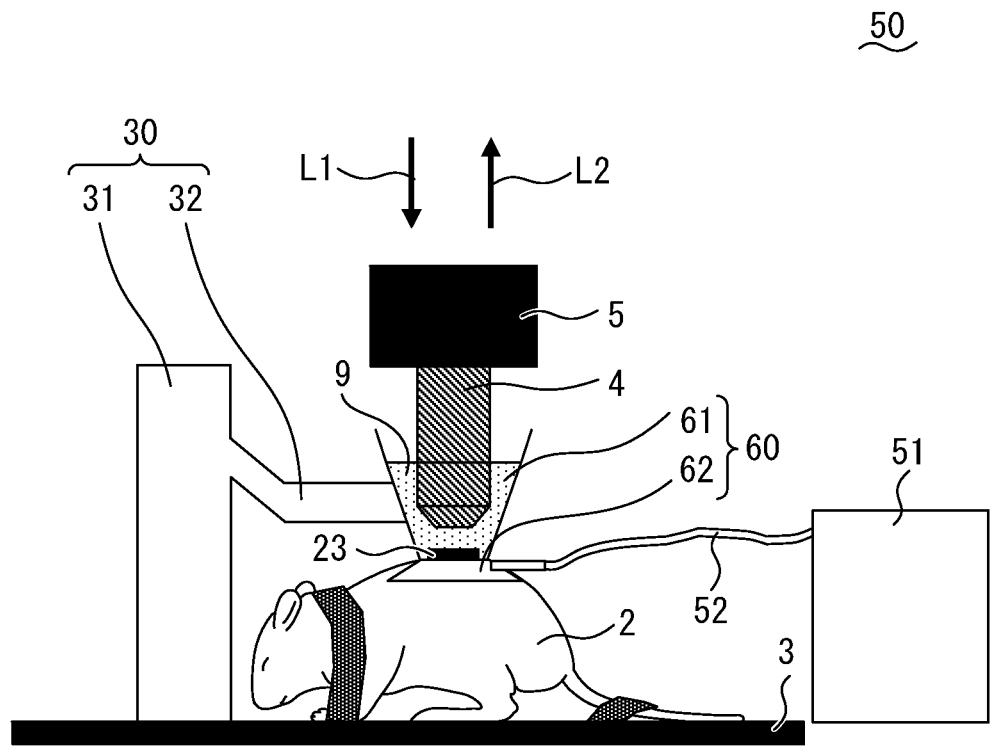
FIG. 6 illustrates a configuration of an observed portion fixing apparatus according to a second embodiment of the present invention.

FIG. 6 illustrates a configuration of an observed portion fixing apparatus according to a second embodiment. The observed portion fixing apparatus 50 according to this embodiment is different from the observed portion fixing apparatus 10 according to the first embodiment in that the observed portion fixing apparatus 50 includes an immersion liquid retainer 60 as a replacement for the immersion liquid retainer 20 and further includes a pump 51 and a tube 52, which are intended to fix the mouse 2 to the immersion liquid retainer 60 with a negative pressure (namely, a pressure state lower than the atmospheric pressure). Moreover, a microscope according to the second embodiment not illustrated is different from the microscope 1 according to the first embodiment in that the microscope according to this embodiment includes the observed portion fixing apparatus 50 as a replacement for the observed portion fixing apparatus 10. The microscope according to this embodiment is similar to the microscope 1 except for this point.

The immersion liquid retainer 60 includes an immersion liquid retaining part 61 for retaining the immersion liquid 9 and a fixing part 62 for fixing an observed portion of the mouse 2. The immersion liquid retainer 60 is similar to the immersion liquid retainer 20 according to the first embodiment in that the cover glass 23 configures a bottom surface of a concave part formed in the immersion liquid retaining part 61.

Figure 7A:
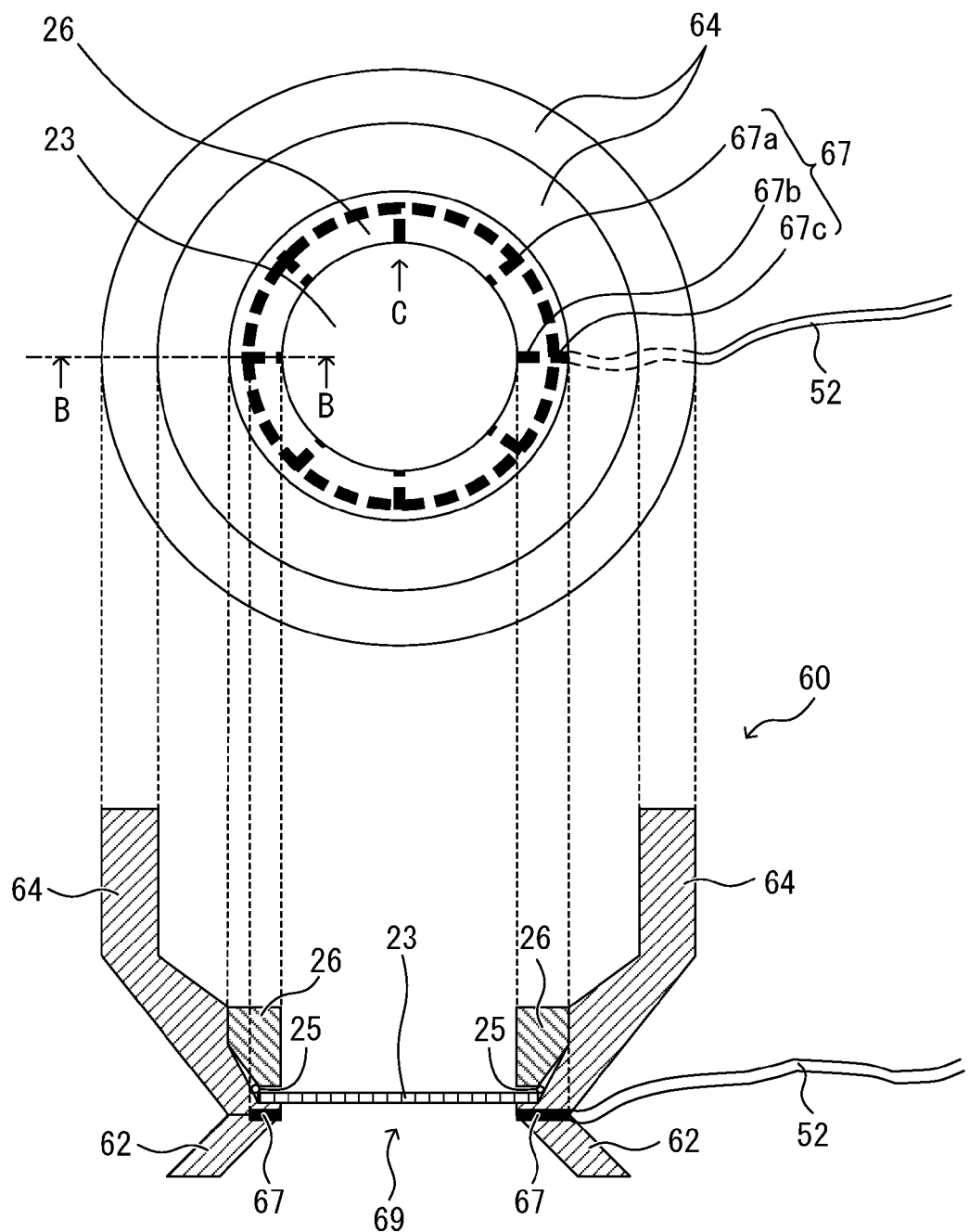
FIG. 7A illustrates a configuration of the immersion liquid retainer according to the second embodiment of the present invention.
Figure 7B:
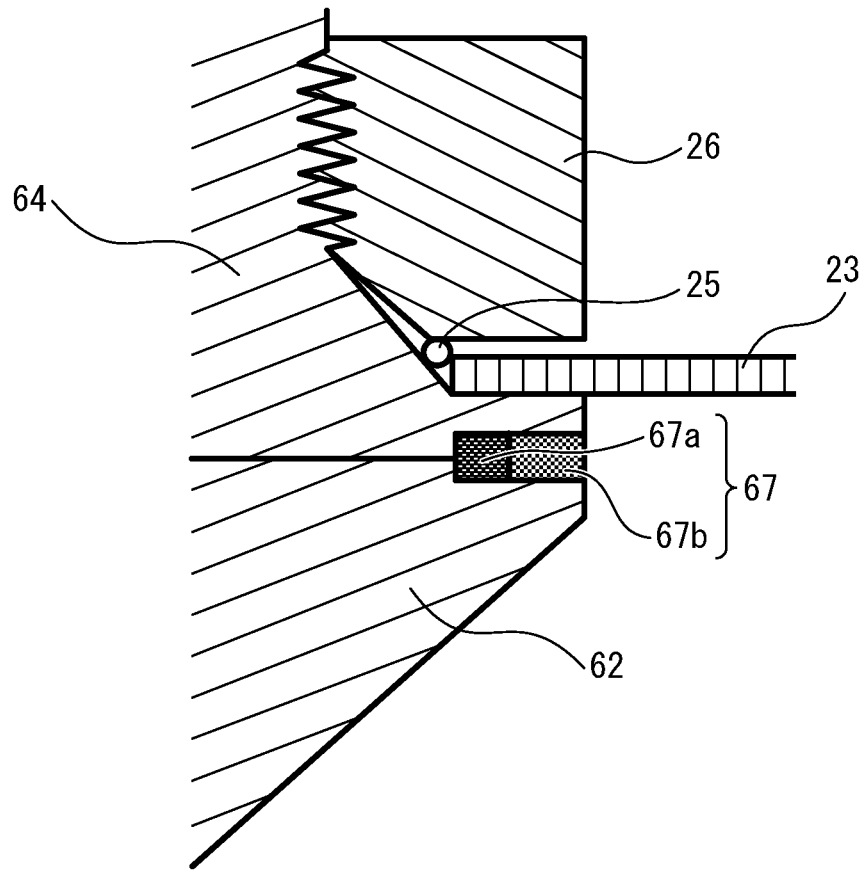
FIG. 7B is a cross-sectional view of the immersion liquid retainer illustrated in FIG. 7A taken along a line B-B.
Figure 7C:
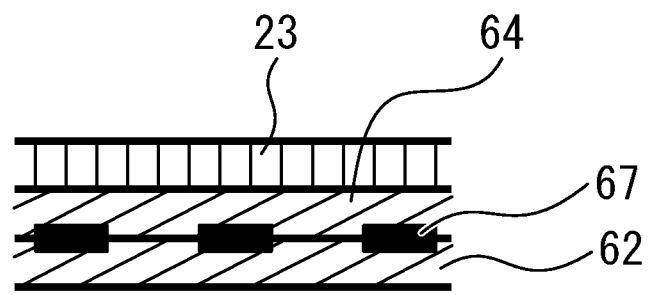
FIG. 7C illustrates the immersion liquid retainer illustrated in FIG. 7A when viewed in a direction of an arrow C.

FIG. 7A illustrates a configuration of the immersion liquid retainer according to this embodiment. This figure illustrates both a top view of the immersion liquid retainer (an upper portion of FIG. 7A) and a cross-sectional view of the immersion liquid retainer (a lower portion of FIG. 7A). FIG. 7B is a cross-sectional view of the immersion liquid retainer illustrated in FIG. 7A taken along a line B-B. FIG. 7C illustrates the immersion liquid retainer illustrated in FIG. 7A when viewed in a direction of an arrow C. The configuration of the immersion liquid retainer 60 included in the observed portion fixing apparatus 50 is described in detail with reference to FIGS. 7A to 7C.

As illustrated in FIGS. 7A and 7B, the immersion liquid retainer 60 is similar to the immersion liquid retainer 20 in that the cover glass 23 is fixed to the immersion liquid retaining part main body 64 with the O-shaped ring 25 and the pressing member 26. The immersion liquid retainer 60 is different from the immersion liquid retainer 20 in that a penetration hole 67 (second penetration hole) penetrating between a space enclosed by the fixing part 62, the cover glass 23 and the mouse 2 and an outer surface of the immersion liquid retainer 60 is formed in addition to the penetration hole 69 (first penetration hole) for viewing an observed portion of the mouse 2 in a state where the immersion liquid retainer 60 is attached to the mouse 2.

The penetration hole 67 is configured with a groove formed on a joint surface for joining the fixing part 62 and the immersion liquid retaining part main body 64 as illustrated in FIGS. 7A to 7C. The penetration hole 67 is, as illustrated by bold dashed line in an upper portion of FIG. 7A, configured with a hole 67a circularly formed around the penetration hole 69 as a center, a hole 67b formed radially from the penetration hole 69 as the center, and a hole 67c penetrating between the hole 67a and the outer surface of the immersion liquid retainer 60.

The tube 52 is linked to the penetration hole 67c, and the pump 51 functions as a suction part for suctioning a gas within a space enclosed by the fixing part 62, the cover glass 23 and the mouse 2 via the penetration hole 67 and the tube 52. As a result, a negative pressure occurs in the above described space and the mouse 2 is absorbed by the cover glass 23 and the fixing part 62, whereby the observed portion is fixed to the immersion liquid retainer 60. Preferably, the suction force of the pump 51 is adjustable.

Accordingly, with the observed portion fixing apparatus 50 according to this embodiment, the immersion liquid 9 can be retained for a long duration similarly to the observed portion fixing apparatus 10 according to the first embodiment, and movements of an observed portion, which are caused by breathing, heartbeat or the like of the mouse during an observation period, can be suppressed with a low pressing force or without applying a pressing force in comparison with the observed portion fixing apparatus 10. Therefore, a burden imposed on the mouse 2 can be reduced.

Figure 8B:
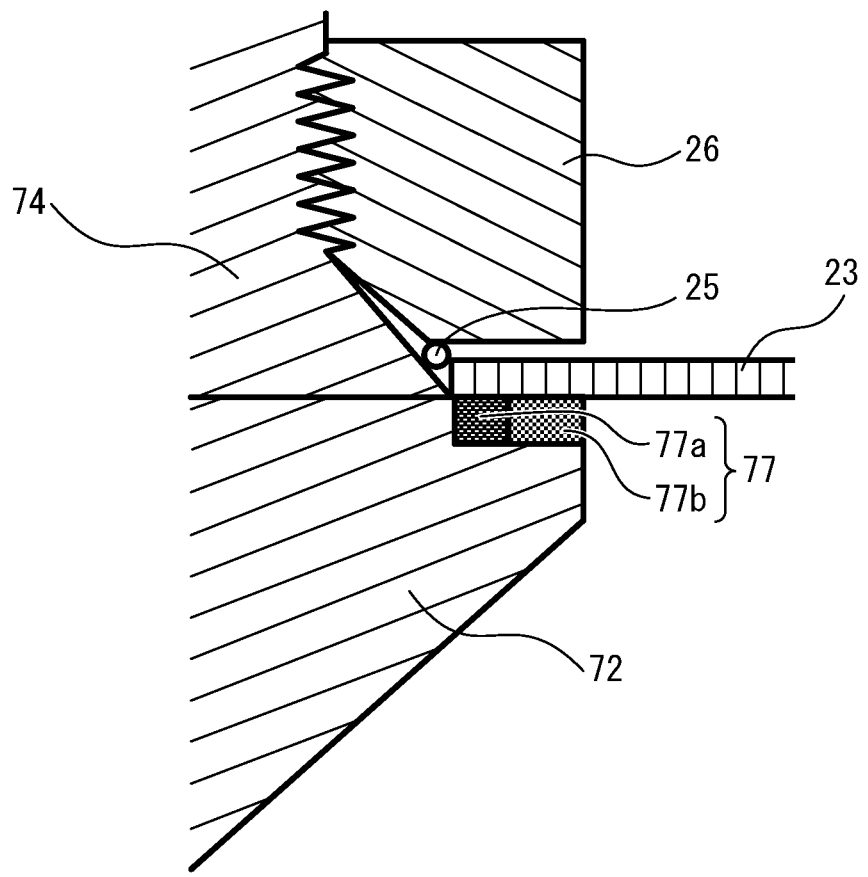
FIG. 8B is a cross-sectional view of the immersion liquid retainer illustrated in FIG. 8A taken along a line B-B.
Figure 8C:
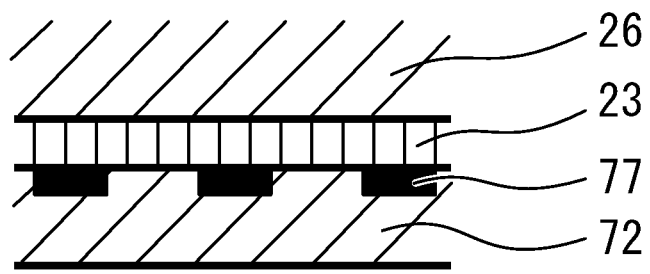
FIG. 8C illustrates the immersion liquid retainer illustrated in FIG. 8A when viewed in a direction of an arrow C.

FIGS. 7A to 7C illustrate the example where the cover glass 23 is arranged on the bottom surface of the concave part of the immersion liquid retaining part main body 64, However, the cover glass 23 may be arranged on a joint surface of a fixing part 72 joined to an immersion liquid retaining part main body 74 as illustrated in FIGS. 8A to 8C. In this case, a penetration hole 77 may be configured with a groove formed on a surface that is a surface of the fixing part 72 and is the same as the surface making contact with the cover glass 23. Similarly to the penetration hole 67, the penetration hole 77 (second penetration hole) may be, as illustrated by bold dashed line in an upper portion of FIG. 8A, configured with a hole 77a formed circularly around the penetration hole 79 (first penetration hole) as a center, a hole 77b formed radially from the penetration hole 79 as the center, and a hole 77c penetrating between the hole 77a and an outer surface of the immersion liquid retainer 70. The penetration hole 77 can be formed at an arbitrary position as long as the pump 51 can suction a gas within the space enclosed by the fixing part, the cover glass 23 and the mouse 2.

<Third Embodiment>

FIG. 9 illustrates a configuration of an observed portion fixing apparatus according to a third embodiment. The observed portion fixing apparatus 80 according to this embodiment is different from the observed portion fixing apparatus 50 according to the second embodiment in that the observed portion fixing apparatus 80 includes a support part 90 as a replacement for the support part 30. Moreover, a microscope according to this embodiment not illustrated is different from the microscope 1 according to the first embodiment in that the microscope according to this embodiment includes the observed portion fixing apparatus 80 as a replacement for the observed portion fixing apparatus 10. The microscope according to this embodiment is similar to the microscope 1 except for this point.

The support part 90 is different from the support part 30 according to the second embodiment in that the support part 90 includes three driving units (driving units 93, 94, and 95) in addition to the support part main body 31 and the arm part 32. The driving units 93, 94, and 95 respectively have a function of moving the immersion liquid retainer 60 relatively to the stage 3 by driving the arm part 32 in their orthogonal direction. The three driving units may be operated manually or electrically.

Figure 10A:
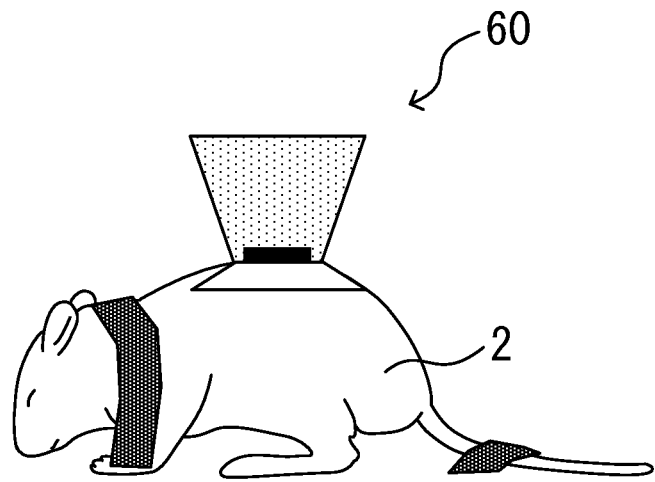
FIG. 10A illustrates one example of an attached position of the immersion liquid retainer.
Figure 10B:
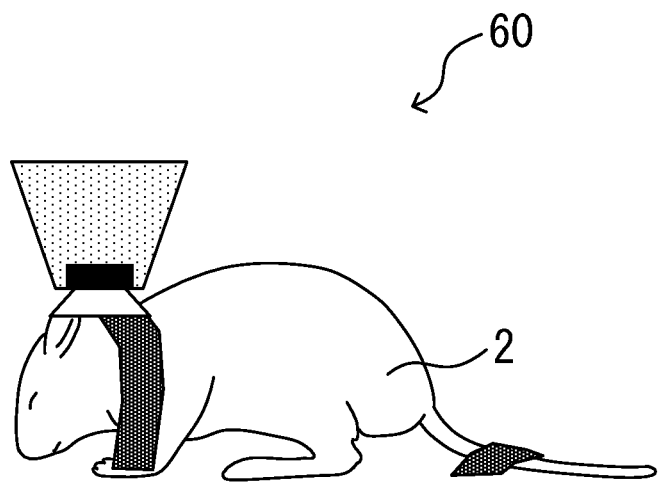
FIG. 10B illustrates another example of the attached position of the immersion liquid retainer.

With the observed portion fixing apparatus 80 according to this embodiment, the position of the immersion liquid retainer 60 is changed relative to the mouse 2 by operating the three driving units, so that the immersion liquid retainer 60 can be attached and fixed to an arbitrary portion of the mouse 2, for example, as illustrated in FIGS. 10A and 10B. Alternatively, the immersion liquid retainer 60 may be attached and fixed to an abdominal area of the mouse 2 by placing the mouse 2 on its back as illustrated in FIG. 10C. Then, the immersion objective 4 can be positioned on the cover glass 23 by moving also the stage 3 with a move of the immersion liquid retainer 60 by the three driving units. The observed portion fixing apparatus 80 is similar to the observed portion fixing apparatus 50 according to the second embodiment in that the immersion liquid 9 can be retained for a long duration, and movements of an observed portion, which are caused by breathing, heartbeat or the like of the mouse 2, can be suppressed with a low pressing force or without applying a pressing force during an observation period.

Figure 11:
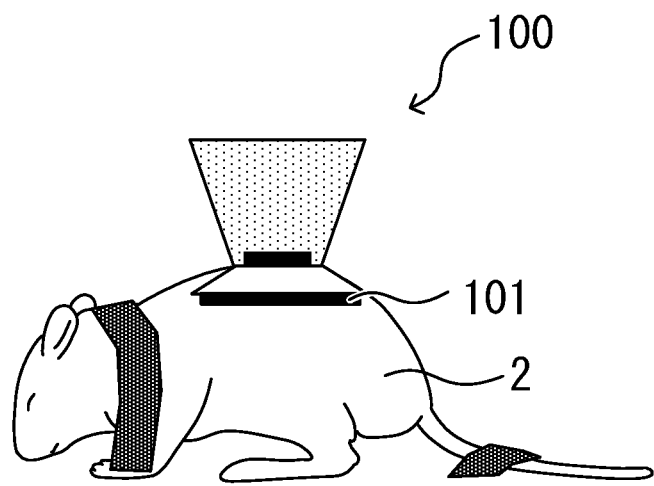
FIG. 11 illustrates a configuration of an immersion liquid retainer according to a fourth embodiment of the present invention.

The first embodiment refers to the example where the immersion liquid retainer is fixed to a specimen with a pressing force, whereas the second and the third embodiments refer to the example where the immersion liquid retainer is fixed to the specimen by absorption or by both a pressing force and absorption. However, the immersion liquid retainer may be fixed to the specimen with another method. For example, an immersion liquid retainer 100 may be fixed to the mouse 2, which is a specimen, with an adhesive 101 as illustrated in FIG. 11.

The above described embodiments refer to the specific examples for ease of understanding of the present invention. However, the present invention is not limited to these embodiments. The immersion liquid retainer, the observed portion fixing apparatus and the microscope according to the embodiments can be modified and changed in a variety of ways in a scope that does not depart from the concept of the present invention stipulated by claims.

What is claimed is:

1. An observed portion fixing apparatus, comprising:
   an immersion liquid retainer used for an observation made with a microscope including an immersion objective, the immersion liquid retainer including:
   an immersion liquid retaining part including a concave part configured to retain an immersion liquid, and a transparent flat plate which forms a bottom of the concave part, and
   a fixing part arranged under the immersion liquid retaining part, the fixing part having a first penetration hole for viewing an observed portion of a specimen, and the fixing part being configured to be fixed to the specimen, wherein the immersion liquid retaining part is joined to the fixing part or formed integrally with the fixing part such that the transparent flat plate covers the first penetration hole; and a support part provided on a stage where the specimen is placed, the support part supporting the immersion liquid retainer, the support part including:
   a support part main body provided on the stage,
   an arm part for supporting the immersion liquid retainer extending from the support part main body, and
   a driving unit for moving the immersion liquid retainer relatively to the stage.

2. The observed portion fixing apparatus according to claim 1, further comprising a suction part for suctioning a gas within a space enclosed by the fixing part, the specimen, and the transparent flat plate,
   wherein the suction part suctions the gas within the space via a second penetration hole formed in the immersion liquid retainer.

3. The observed portion fixing apparatus according to claim 2, wherein the second penetration hole is configured with a groove formed on a surface that is a surface of the fixing part and is the same as a surface making contact with the transparent flat plate.

4. The observed portion fixing apparatus according to claim 2, wherein the second penetration hole is configured with a groove formed on a joint surface for joining the fixing part and the immersion liquid retainer.

5. The observed portion fixing apparatus according to claim 1, wherein the driving unit moves the immersion liquid retainer relative to the stage by driving the arm part.

6. A microscope, comprising:
   the observed portion fixing apparatus according to claim 1;
   an immersion objective immersed in an immersion liquid retained in the immersion liquid retainer of the observed portion fixing apparatus; and
   a stage on which a specimen is placed.

7. The microscope according to claim 6, wherein an inner diameter of the concave part of the immersion liquid retaining part is larger than an outer diameter of a tip of the immersion objective.

8. The observed portion fixing apparatus according to claim 1, wherein
   the concave part formed in the immersion liquid retaining part stores the immersion liquid so as to immerse a tip of the immersion objective in the immersion liquid from below.

9. The observed portion fixing apparatus according to claim 1, wherein
   the fixing part has the first penetration hole at a top part thereof, and the fixing part increases in width from the top part to a bottom part.

* * * * *